(12) United States Patent
Vehring et al.

(10) Patent No.: US 8,668,934 B2
(45) Date of Patent: Mar. 11, 2014

(54) PHARMACEUTICAL FORMULATION COMPRISING A WATER-INSOLUBLE ACTIVE AGENT

(75) Inventors: Reinhard Vehring, Belmont, CA (US); Danforth P Miller, San Carlos, CA (US); David Lechuga-Ballesteros, San Jose, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/953,259

(22) Filed: Nov. 23, 2010

(65) Prior Publication Data

US 2011/0070309 A1 Mar. 24, 2011

Related U.S. Application Data

(62) Division of application No. 10/855,798, filed on May 27, 2004, now Pat. No. 7,862,834.

(60) Provisional application No. 60/474,087, filed on May 28, 2003.

(51) Int. Cl.
| | | |
|---|---|---|
| A61K 9/00 | (2006.01) | |
| A61K 9/12 | (2006.01) | |
| A61P 31/00 | (2006.01) | |
| A61P 29/00 | (2006.01) | |
| A61P 11/00 | (2006.01) | |

(52) U.S. Cl.
USPC ........... 424/489; 424/400; 424/469; 514/772; 264/14

(58) Field of Classification Search
USPC .............. 424/489, 400, 469; 514/772; 264/14
See application file for complete search history.

(56) References Cited

U.S. PATENT DOCUMENTS

| 4,016,254 A * | 4/1977 | Seager .................... 424/497 |
| 4,995,385 A | 2/1991 | Valentini et al. |
| 5,378,474 A | 1/1995 | Morella et al. |
| 5,500,227 A | 3/1996 | Oshlack et al. |
| 5,622,657 A | 4/1997 | Takada et al. |
| 5,648,096 A | 7/1997 | Gander et al. |

(Continued)

FOREIGN PATENT DOCUMENTS

| WO | 96/09814 | 4/1996 |
| WO | 96/32149 | 10/1996 |

(Continued)

OTHER PUBLICATIONS

Encyclopedia of Pharmaceutical Technology, vol. 20, editors: James Swarbrick, James C. Boylan, 2001, p. 98.*

(Continued)

*Primary Examiner* — Aradhana Sagan
(74) *Attorney, Agent, or Firm* — Janah & Associates, PC (57) ABSTRACT

A method of preparing a pharmaceutical formulation comprises providing a solution comprising a first solvent, a second solvent, an active agent, and an excipient. The second solvent is less polar than the first solvent and the excipient is more soluble in water than the active agent. The first and second solvents are removed from the solution to produce particles comprising the active agent and the excipient. In one version, the excipient comprises an amino acid and/or a phospholipid. A pharmaceutical formulation made by a version of the invention comprises particles comprising an active agent and an excipient which at least partially encapsulates the active agent, wherein the excipient is more soluble in water than the active agent.

23 Claims, 4 Drawing Sheets

(56) References Cited

U.S. PATENT DOCUMENTS

| | | | |
|---|---|---|---|
| 5,651,990 | A | 7/1997 | Takada et al. |
| 5,667,806 | A | 9/1997 | Kantor |
| 5,723,269 | A | 3/1998 | Akagi et al. |
| 5,928,469 | A | 7/1999 | Franks et al. |
| 5,976,574 | A | 11/1999 | Gordon |
| 5,985,248 | A | 11/1999 | Gordon et al. |
| 5,993,805 | A | 11/1999 | Sutton et al. |
| 6,001,336 | A | 12/1999 | Gordon |
| 6,051,256 | A | 4/2000 | Platz et al. |
| 6,077,543 | A | 6/2000 | Gordon et al. |
| 6,136,346 | A | 10/2000 | Eljamal et al. |
| 6,149,941 | A | 11/2000 | Schwarz et al. |
| 6,165,511 | A | 12/2000 | Schwarz et al. |
| 6,258,341 | B1 | 7/2001 | Foster et al. |
| 6,309,671 | B1 | 10/2001 | Foster et al. |
| 6,358,530 | B1 | 3/2002 | Eljamal et al. |
| 6,372,258 | B1 | 4/2002 | Platz et al. |
| 6,423,344 | B1 | 7/2002 | Platz et al. |
| RE37,872 | E | 10/2002 | Franks et al. |
| 6,475,523 | B1 | 11/2002 | Staniforth |
| 6,503,927 | B1 | 1/2003 | Ronsen et al. |
| 6,518,239 | B1 | 2/2003 | Kuo et al. |
| 6,582,728 | B1 | 6/2003 | Platz et al. |
| 6,582,729 | B1 | 6/2003 | Eljamal et al. |
| 6,586,008 | B1 | 7/2003 | Batycky et al. |
| 6,835,372 | B2 | 12/2004 | Kuo |
| 2001/0036481 | A1 | 11/2001 | Basu |

FOREIGN PATENT DOCUMENTS

| | | |
|---|---|---|
| WO | WO 9703649 | 2/1997 |
| WO | 97/13053 | 4/1997 |
| WO | WO 9713503 | 4/1997 |
| WO | 98/16205 | 4/1998 |
| WO | 98/47493 | 10/1998 |
| WO | 99/16419 | 4/1999 |
| WO | 00/10541 | 3/2000 |
| WO | 01/00312 | 1/2001 |
| WO | WO 0113891 | 3/2001 |
| WO | WO 03043585 | 3/2001 |
| WO | 01/85136 | 11/2001 |
| WO | 02/00197 | 1/2002 |
| WO | 02/09669 | 2/2002 |
| WO | 02/067902 | 9/2002 |
| WO | 03/035028 | 5/2003 |
| WO | 03/072080 | 9/2003 |
| WO | 03/080028 | 10/2003 |
| WO | 2004/060351 | 7/2004 |

OTHER PUBLICATIONS

T.G. Fox, "Second-Order Transition Temperatures and Related Properties of Polystrene. I. Influence of Molecular Weight", J. Applied Physics, 21:581-591.

PDR®, 49$^{th}$ ed, p. 572 (1995).

Smale Nick "Clean up with pulsed jets" *Mfg Chem* pp. 29-31 (1992).

International Search Report, PCT/US2004/016696 (Dec. 22, 2004).

Wolfer Opinion, PCT/US2004/016696 (Dec. 1, 2005).

\* cited by examiner

PHARMACEUTICAL FORMULATION COMPRISING A WATER-INSOLUBLE ACTIVE AGENT

This is a divisional of application Ser. No. 10/855,798 (pending) filed on May 27, 2004, which claims the benefit of U.S. Provisional Application No. 60/474,087 filed May 28, 2003, the entire disclosures of which are hereby incorporated by reference.

BACKGROUND

The present invention relates generally to particulate drug delivery compositions comprising water-insoluble active agents and their methods of production. The invention is particularly suited for producing particles for pharmaceutical applications.

The need for effective therapeutic treatment of patients has resulted in the development of a variety of pharmaceutical formulation delivery techniques. One traditional technique involves the oral delivery of a pharmaceutical formulation in the form of a pill, capsule, elixir, or the like. However, oral delivery can in some cases be undesirable. For example, many pharmaceutical formulations may be degraded in the digestive tract before they can be effectively absorbed by the body. Inhaleable drug delivery, where an aerosolized pharmaceutical formulation is orally or nasally inhaled by a patient to deliver the formulation to the patient's respiratory tract, has proven to be a particularly effective and/or desirable alternative. For example, in one inhalation technique, an aerosolized pharmaceutical formulation provides local therapeutic treatment or prophylaxis to a portion of the respiratory tract, such as the lungs, to treat diseases of the lung such as asthma, emphysema, and cystic fibrosis. In another inhalation technique, a pharmaceutical formulation is delivered deep within a patient's lungs where it may be absorbed into the blood stream for systemic treatment or prophylaxis of a disease.

Many types of aerosolization devices exist including devices that aerosolize a dry powder pharmaceutical formulation, devices comprising a liquid or powder pharmaceutical formulation stored in or with a propellant, devices which use a compressed gas to aerosolize a liquid or suspension pharmaceutical formulation, and similar devices. However, the formulation of stable and reproducibly aerosolizable water-insoluble active agents has proven to be a difficult task. For example, liquid formulations comprising insoluble active agents may not be delivered in sufficiently high concentrations for easy dosing of a therapeutic agent. Previous attempts at producing pharmaceutical formulations comprising insoluble drugs include size reduction of drug crystals by micronization, milling, high pressure homogenization, and ultrasound or the development of drug delivery vehicles to solubilize or complex the poorly soluble drug, such as by using emulsions, microemulsions, solid lipid nanoparticles, and cyclodextrins. However, these solutions are often prohibitively costly and often produce poor results.

One technique for forming a pharmaceutical formulation comprising an insoluble active agent involves the incorporation of small particles of the insoluble active agent in a matrix material, as described in PCT/US2003/041703 which is incorporated herein by reference in its entirety. The matrix material is then suspended in a liquid feedstock which is spray dried to form solid particles comprising the matrix material and the particles of insoluble active agent. However, this process often involves the step of milling or otherwise reducing the size of the active agent particles. For some active agents, it is difficult to reduce the size a desired amount. In addition, for some active agents, the size reduction process may alter the active agent and decrease the stability of the active agent.

Spray drying of feedstocks comprising hydrophobic active agent and/or co-solvents such as ethanol and water have been described, for example, in U.S. Pat. Nos. 5,976,574, 5,985,248, and 6,001,336, all of which are incorporated herein by reference in their entireties. However, the co-solvent spray drying of some poorly water-soluble active agents often results in particles having which have less than optimal particle characteristics. For example, due to the limited selection of suitable excipients that may be used in the formulation, particles comprising poorly water-soluble active agents that have been produced by co-solvent spray drying have shown less than desirable aerosolization characteristics.

In addition, it is also sometimes desirable to provide particles that comprise an active agent coated with a coating layer. The coating layer may be useful in improving the dispersibility of the particles. Coating layers may also be provided for masking the taste of an active agent when the active agent is being administered in an oral dosage form, as an oral dissolving tablet, or as an aerosolizable powder. Coatings may also be applied to active agents in order to provide sustained release properties to the active agent. However, it has been difficult to coat water-insoluble active agents.

Therefore, it is desirable to be able to prepare a pharmaceutical formulation comprising a water-insoluble active agent and a more water soluble excipient. It is further desirable to formulate the water-insoluble active agent in a highly dispersible, aerosolizeable, and/or coated manner. It is further desirable to formulate the water-insoluble active agent in a manner that increases the stability of the active agent.

SUMMARY

The present invention satisfies these needs. In one aspect of the invention an improved method is provided for producing particles comprising a water-insoluble active agent.

In one aspect of the invention, a method of preparing a pharmaceutical formulation comprises providing a solution comprising a first solvent, a second solvent, an active agent, and an excipient, wherein the second solvent is less polar than the first solvent, wherein the excipient is more soluble in water than the active agent, and wherein the excipient comprises an ammo acid and/or a phospholipid; and removing the first and second solvents to produce particles comprising the active agent and the excipient.

In another aspect of the invention, a method of preparing an aerosolizable pharmaceutical formulation comprises providing a solution comprising a first solvent, a second solvent, an active agent, and an excipient, wherein the second solvent is less polar than the first solvent and wherein the excipient is more soluble in water than the active agent; and removing the first and second solvents to produce particles comprising the active agent and the excipient, wherein at least 20% of the particles have an aerodynamic diameter less than 3.3 μm when determined gravimetrically in an Anderson Cascade Impactor.

In another aspect of the invention, a pharmaceutical formulation comprises particles comprising an active agent and an excipient at least partially encapsulating the active agent, wherein the excipient is more soluble in water than the active agent.

In another aspect of the invention, a pharmaceutical formulation is made by a method comprising providing a solution comprising a first solvent, a second solvent, an active agent, and an excipient, wherein the second solvent is less polar than the first solvent and wherein the excipient is more soluble in water than the active agent; and removing the first and second solvents to produce particles comprising the active agent and the excipient, wherein at least 20% of the particles have an aerodynamic diameter less than 3.3 μm when determined gravimetrically in an Anderson Cascade Impactor.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

FIGS. 1*a*-1*c* are schematic sectional side views of particle morphologies according to an aspect of the present invention;

FIG. 2 is a block diagram schematically illustrating primary unit operations of a spray-drying process useful according to an aspect of the invention;

FIG. 3 is a detailed schematic diagram illustrating a spray-drying useful according to an aspect of the invention;

FIG. 4 is a SEM depicting particles comprising budesonide and leucine made according to a version of the invention;

FIG. 5 is a SEM depicting neat budesonide particles according to a comparative example; and FIG. 6 is a SEM depicting particles comprising budesonide and leucine made according to another version of the invention.

DESCRIPTION

The present invention relates to particulate drug delivery compositions comprising water-insoluble active agents and their methods of production. The invention is particularly suited for producing particles for pharmaceutical applications. Although the process is illustrated in the context of pharmaceutical formulations for aerosolization and oral applications, the present invention can be used in other processes and should not be limited to the examples provided herein.

DEFINITIONS

As used herein, "active agent" as includes an agent, drug, compound, composition of matter or mixture thereof which provides some pharmacologic, often beneficial, effect. The effect may be a therapeutic effect, such as a treatment effect or a prophylactic effect. This includes feeds, feed supplements, nutrients, drugs, vaccines, vitamins, and other beneficial agents. As used herein, "active agent" includes any physiologically or pharmacologically active substance that produces a localized or systemic effect in a patient. The active agent that can be delivered includes, for example, antibiotics, antifungal agents, antiviral agents, anepileptics, analgesics, anti-inflammatory agents, bronchodilators, and viruses and may be inorganic and organic compounds, including, without limitation, drugs which act on the peripheral nerves, adrenergic receptors, cholinergic receptors, the skeletal muscles, the cardiovascular system, smooth muscles, the blood circulatory system, synaptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, psychic energizers, tranquilizers, anticonvulsants, muscle relaxants, antiparkinson agents, anti-inflammatories, muscle contractants, antimicrobials, antimalarials, hormonal agents including contraceptives, sympathomimetics, polypeptides, and proteins capable of eliciting physiological effects, diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

Examples of active agents useful in this invention include but are not limited to actives for respiratory indications, such as bosentan, formoterol, loratidine, salmeterol, steroids and their salts, such as budesonide, testosterone, methyl testosterone, progesterone, dihydro epiandrosterone, medroxyprogesterone, estrogen, flunisolide, triamcinolone, beclomethasone, betamethasone, dexamethasone, fluticasone, mometasone, methylprednisolone, prednisone, hydrocortisone, and the like; peptides, such as cyclosporin and other water-insoluble peptides; retinoids, such as all cis-retinoic acid, all-trans-retinoic acid, 13-trans retinoic acid, and other vitamin A and beta carotene derivatives; vitamins D, E, and K and water-insoluble precursors and derivatives thereof; prostagladins and leukotrienes and their activators and inhibitors including prostacyclin (epoprostanol), and prostaglandins $E_1$ and $E_2$; tetrahydrocannabinol, methadone, nicotine, amphetamine; lung surfactant lipids, lipid soluble antioxidants; anti-infective and chemotherapeutic drugs, such as acyclovir, adriamycin, albendazole, amphotericin B, amprenavir, azithromycin, cefdinir, ceftixime, ceftazidime, ciprofloxacin, clarithromycin, didanosine, dirithromycin, efavirenz, ganciclovir, gentamicin, intraconazole, itraconazole, ketoconazole, mefloquine, metronidazole, miconazole, nelfinavir, norfloxacin, ritonavir, saquinavir, tenofovir, voriconazole; CNS active agents, such as clozapine, clonazepam, entacapone, fluphenazine decanoate, fluvoxamine, imipramine, midazolam, olanzapine, paroxetine, sertraline, sulpiride, triazolam, zaleplon; ergotamine, dihydroergotamine, ergotamine tartrate, ergoloid, ergotamine fentanyl; triptans and their salts, such as sumatriptan, zolmitriptan, rizatriptan, naratriptan, eletriptan, almotriptan, frovatriptan, and the like; leukotriene receptor antagonists, such as zaflrlukast, montelukast, and zileuton; analgesics, such as celecoxib, diclofenac, ibuprofen, nabumetone, tramadol; active agents for cardiovascular indications, such as alendronate, amiodarone, candesartan, carvedilol, clopidogrel, dipyridamol, eposartan, felodipine, furosemide, isradipine, metolazone, propafenone, quinapril, ramipril, spironolactone, trandolapril, valsartan; statins, such as cerivistatin, pravastatin, simvastatin, fluvastatin, atorvastatin, lovastatin; actives used in oncology and immune suppression, such as azathioprin, carboplatin IV, cisplatin, docetaxel, epotoside, fluorouracil, irinotecan, letrozole, melphalan, mitotane, paclitaxel, pimecrolimus, sirolimus, tacrolimus, valrubicin; other actives: acutretin, aminogluthemide, amphetamine, atovaquone, baclofen, benezepril, benzonatate, bicalutanide, bupropion, busulphan, butenafine, calcifediol, calciprotiene, calcitriol, camptothecan, carbamezepine, carotene, chlorpheniramine, cholecalciferol, cilostazol, cimetidine, cinnarizine, cisapride, citrizine, clemastine, clomiphene, clomipramine, codeine, dantrolene, dexchlopheniramine, dicoumarol, digoxin, dihydrotachysterol, donepezil, dronabinol, ergocalciferol, ethinyl estradiol, etodolac, etoposide, danazol, famotidine, fenofibrate, fentanyl, fexofenadine, finasteride, flucanazole, flurbiprofen, follitropin, fosphenytion, furazolidone, gabapentin, gemfibrozil, glibenclamide, glipizide, glyburide, glymepride, griseofulvin, halofantrine, irbesartan, isosorbidedinatrate, isotretinoin, ivermectin, ketorolac, lamotrigine, lanosprazole, leflunomide, lisinopril, loperamide, L-thryroxine, mefepristone, megestrol, methoxsalen, miglitol, minoxidil, mitoxantrone, modafinil nimodipine, nalbuphine, nifedipine, nilsolidipine, nilutanide, nitrofurantoin, nizatidine, omeprazole, oprevelkin, osteradiol, oxaprozin, paricalcitol, pentazocine, pioglitazone, pizofetin, probucol, propofol, pseudo-ephedrine, pyridostigmine, rabeprazole, raloxifene, refocoxib, repaglinide, rifabutine, rifapentine, rimexolone, rosigiltazone, sibutramine, sildenafil, tacrine, tamoxifen, tamsulosin, targretin, tazarotene, telmisartan, teniposide, terbinafine, terzosin, thalidomide, tiagabine, ticlidopine, tirofibran, tizanidine, topiramate, topotecan, toremifene, tretinoin, troglitazone, trovafloxacin, venlafaxine, vertoporfin, vigabatrin, zolpidem, zopiclone, and combinations thereof. The active agents may be in various forms, such as charged or uncharged molecules, components of molecular complexes or pharmacologically acceptable salts. The active agents may be naturally occurring molecules or they may be recombinantly produced, or they may be analogs of the naturally occurring or recombinantly produced active agents with one or more amino acids added or deleted.

The active agent of the present invention may be combined with pharmaceutical carriers or excipients. Such carriers or excipients may serve simply as bulking agents when it is desired to reduce the active agent concentration in the powder which is being delivered to a patient, or may be added to the active agent prior to processing for taste masking and/or to improve the stability and/or dispersibility of the powder. In other embodiments, the excipients may be delivered via the pulmonary route without an active agent, for example in clinical trials as a placebo. Such excipients include but are not limited to (a) carbohydrates, e.g., monosaccharides such as fructose, galactose, glucose, D-mannose, sorbose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; (b) amino acids, such as alanine, praline, glycine, arginine, aspartic acid, glutamic acid, cysteine, lysine, leucine, tri-leucine and the like; (c) organic salts prepared from organic acids and bases, such as sodium citrate, sodium ascorbate, magnesium gluconate, sodium gluconate, tromethamine hydrochloride, and the like; (d) peptides and proteins such as aspartame, human serum albumin, gelatin, and the like; (e) alditols, such as mannitol, xylitol, and the like; (f) biodegradable polymers such as polyvinylpyrrolidone or cellulose derivatives, and (g) surfactants including fluorinated and nonfluorinated compounds such as saturated and unsaturated lipids, nonionic detergents, nonionic block copolymers, ionic surfactants and combinations thereof. A preferred group of excipients includes lactose, trehalose, raffinose, maltodextrins, glycine, alanine, proline, leucine, tri-leucine, sodium citrate, human serum albumin, mannitol, and phospholipids from both natural and synthetic sources that preferably have a gel to liquid crystal phase transition greater than about 40° C. Preferred phospholipids are relatively long chain (i.e. $C_{16}$-$C_{22}$) saturated lipids and more preferably comprise saturated phospholipids, most preferably saturated phosphatidylcholines having acyl chain lengths of 16:0 or 18:0 (palmitoyl and stearoyl). Exemplary phospholipids include phosphoglycerides such as dipalmitoylphosphatidylcholine, disteroylphosphatidylcholine, diarachidoylphosphatidylcholine, dibehenoylphosphatidylcholine, diphosphatidyl glycerol, short-chain phosphatidylcholines, long-chain saturated phosphatidylethanolamines, long-chain saturated phosphatidylserines, long-chain saturated phosphatidylglycerols, and long-chain saturated phosphatidylinositols.

As used herein, the term "dry" means that the particles of a powder have a moisture and/or residual solvent content such that the powder is physically and chemically stable in storage at room temperature. In certain embodiments, the moisture and residual solvent content of the particles is below 10% by weight. In specific embodiments, the moisture content may be below 5% by weight, below 3% by weight, below 2% by weight, or even below about 1% by weight or lower. The moisture and residual solvent content will usually be controlled by the drying conditions, as described in more detail below.

As used herein, the term "emitted dose" or "ED" refers to a measure of the delivery of dry powder from a suitable inhaler device after a firing or dispersion event from a powder unit or reservoir. ED is defined as the ratio of the dose delivered by an inhaler device (described in detail below) to the nominal dose (i.e., the mass of powder per unit dose placed into a suitable inhaler device prior to firing). The ED is an experimentally-determined amount, and is typically determined using an in-vitro device set up which mimics patient dosing. To determine an ED value, a nominal dose of dry powder (as defined above) is placed into a suitable dry powder inhaler, which is then actuated, dispersing the powder. The resulting aerosol cloud is then drawn by vacuum from the device, where it is captured on a tared filter attached to the device mouthpiece. The mass of powder that reaches the filter constitutes the delivered dose. For example, for a 5 mg, dry powder-containing blister pack placed into an inhalation device, if dispersion of the powder results in the recovery of 4 mg of powder on a tared filter as described above, then the ED for the dry powder composition is: 4 mg (delivered dose)/5 mg (nominal dose)×100%=80%. Compositions according to the present invention comprise emitted doses of at least 40%, preferably at least 60%, and most preferably at least 75%.

As used herein, the term "mass median aerodynamic diameter" ("MMAD") is a measure of the aerodynamic size of a dispersed aerosol particle. The aerodynamic diameter is used to describe an aerosolized particle in terms of its settling behavior, and is the diameter of a unit density sphere having the same settling velocity, generally in air, as the particle in question. The aerodynamic diameter encompasses particle shape, density, and physical size. MMAD refers to the midpoint or median of the aerodynamic particle size distribution of an aerosolized collection of particles determined by cascade impaction. The ultrafine dry powders of the present invention preferably comprise an MMAD within 1-5 µm.

As used herein, the term "passive dry powder inhaler" refers to an inhalation device which relies upon the patient's inspiratory effort to disperse and aerosolize a drug formulation contained within the device and does not include inhaler devices which comprise a means for providing energy to disperse and aerosolize the drug formulation, such as pressurized gas and vibrating or rotating elements.

As used herein, the phrase "ultrafine dry powder" means a powder composition comprising a plurality of discrete, dry particles having the characteristics set forth below. In particular, the dry particles will have an average particle size below 50 µm, preferably below 10 µm, and most preferably below 5 µm, such as in the range from 0.4-5 µm. The average particle size of the powder is measured as mass median diameter (MMD) by conventional techniques. The powders are capable of being readily dispersed in an inhalation device and subsequently inhaled by a patient so that the particles are able to penetrate into the lungs. Alternatively, the ultrafine dry powders are capable of being readily dispersed into individual particulates from an oral dosage form when administered orally.

The ultrafine dry powder compositions produced by embodiments of the invention may have particle size distributions that enable them to target the alveolar region of the lung for pulmonary delivery of systemically acting drugs and/or target the central lung and upper airways for locally acting drugs. Such compositions advantageously may be incorporated into unit dosage and other forms without further size classification. In one embodiment, the ultrafine dry powders have a size distribution where at least 90% of the powder by weight comprises particles having an average size in the range from 0.1 µm to 7 µm, with preferably at least 95% being in the range from 0.4 µm to 5 µm. Additionally, in this embodiment, it is desirable that the particle size distribution avoid having an excess amount of particles with very small average diameters, i.e., below 0.4 µm or larger diameters, i.e. above 10 µm.

As used herein, the term "water-insoluble active agent" or "insoluble active agent" refers to an active agent having a solubility in water at 25° C. of less than 5 mg/ml, preferably below 1 mg/ml, and most preferably less than 0.1 mg/ml.

DETAILED DESCRIPTION

According to the present invention, a pharmaceutical formulation comprising a water-insoluble active agent is prepared. In one version, the water-insoluble active agent and one or more excipients are dissolved or partially dissolved in a liquid or slurry. The liquid is then removed to form particles comprising the water-insoluble active agent and the excipient. In one version, the excipient is more water soluble than the active agent. In this version, the liquid comprises two or more solvents in a ratio selected to optimally dissolve the insoluble active agent and the excipient.

In one version, the liquid comprises a first solvent and a second solvent, the first solvent having a relatively high polarity and the second solvent having a lower polarity than the first solvent. For example, in one version, the first solvent comprises water and/or an organic acid, such as acetic acid, and the second solvent comprises an alcohol, an amine, an aldehyde, a ketone, an ester, a halide, an aromatic, and/or an alkane. In one version, the first solvent comprises water and the second solvent comprises a hydroxylic solvent, such as a C1-C6 alcohol, or acetone. In one particular version, the first solvent is water and the second solvent is ethanol, in a proportion selected to optimally dissolve the active agent and the one or more excipients.

Once the solution is formed, the liquid may be removed from the solution to form particles comprising the active agent and the one or more excipients. For example, the liquid may be removed by spray drying the liquid, by freeze drying the liquid, by liquid extraction, or by causing the particles to precipitate out of the solution. The liquid removal conditions may be selected to produce particles having desired characteristics.

According to one version of the present invention, the particles comprising water-insoluble active agents are prepared by spray drying. Spray drying processes for producing fine powders for inhalation are disclosed in U.S. Pat. Nos. 5,976,574; 5,985,248; 6,001,336; 6,051,256; 6,077,543; 6,423,344; 5,622,657; 5,723,269; 6,149,941; and 6,165,511 and in PCT Publications WO 96/32149; WO 99/16419; WO 01/00312; WO 01/85136; WO 02/09669; and WO 97/13503, all of which are incorporated herein by reference in their entireties. Spray drying is a processing unit operation used to produce dry particulate solids from a variety of liquid and slurry starting materials. In the present invention, the liquid or slurry starting material comprises the first and second solvents discussed above, the water-insoluble active agent and optionally one or more excipients. The first and second solvents are maintained at compositions at or near azeotropic compositions during the spray drying process in order to impart desired particle characteristics into the dried powders. Control over the azeotropic condition of the feedstock is provided through formulation of the feedstock based upon the spray drying process parameters, or alternatively, by setting the spray drying process parameters based upon the feedstock formulation.

Control of the spray-drying process with the co-solvent system according to this embodiment of the present invention allows the engineering of desirable particle characteristics into the dried powders. For example, particle characteristics such as stability, dispersibility, tastemasking, bioavailability, and/or controlled release can be tailored to the powder depending on the desired application. The compositions of the present invention can be used for a variety of drug delivery applications including pulmonary, oral, topical, or injectable.

The processability of the particles and/or the aerosolizability of the particles may be improved by adding a dispersibility enhancing agent to the particle. Accordingly, in one version, the water-insoluble active agent and an excipient comprising a dispersibility enhancing agent are dissolved in the first and second solvents and the liquid is removed from the solution to provide particles comprising the water-insoluble active agent and the dispersibility enhancing agent. It has been discovered that particularly useful dispersibility enhancing agents are amino acids and/or a phospholipids, such as one or more of alanine, leucine, trileucine, dipalmitoylphosphatidylcholine, and disteroylphosphatidylcholineare. Additional dispersibility enhancing agents are disclosed in PCT WO 96/32149 and U.S. Pat. Nos. 6,358,530, 6,372,258 and 6,518,239, all of which are incorporated herein by reference in their entireties.

In another version of the invention, the water-insoluble active agent is formulated in a manner to increase its storage stability. According to this version, the formulation of the liquid feedstock is determined based upon physico-chemical characteristics of the active agent and/or excipients and the drying conditions of the spray drying process. The glass transition temperature, $T_g$, of the active agent is measured by differential scanning calorimetry (DSC) or other known analytical techniques. Based on this $T_g$, and the solubility of the active agent, a glass stabilization excipient is selected. The amount of glass stabilization excipient necessary to increase the $T_g$ to greater than 55° C., preferably greater than 70° C., is calculated using commonly accepted equations such as the Fox equation (Fox, T. G. J. Appl. Phys. 21: 581-591 (1950). This allows estimation of a glass stabilization excipient/active agent ratio, $R_1$, for the dried particles. Active agents which have a suitable $T_g$ on their own can be formulated without any glass stabilization excipient, resulting in a value of zero for $R_1$. Thus $R_1$ is within the range $0 \leq R_1 < 30$.

Glass stabilization excipients suitable for use with the present invention typically have a $T_g$ of at least 55° C., preferably at least 75° C., most preferably at least 100° C., and are pharmaceutically acceptable. According to a preferred embodiment directed to ethanol/water co-solvent systems, suitable glass formers comprise a solubility of greater than 1 mg/ml, more preferably greater than 20 mg/ml in the ethanol/water co-solvent system. Suitable glass formers include, but are not limited to, one or more of trileucine, sodium citrate, sodium phosphate, ascorbic acid, polyvinyl pyrrolidone, mannitol, sucrose, trehalose, lactose, proline, and povidone.

Examples of additional glass-forming excipients are disclosed in U.S. Pat. Nos. RE 37,872, 5,928,469, 6,258,341, and 6,309,671, all of which are incorporated herein by reference in their entireties.

The co-solvent system ratio necessary to (a) dissolve the desired amount of glass stabilization excipient and active agent provided at ratio $R_1$, and to (b) maintain the co-solvent ratio throughout the course of the evaporation until the active agent and the glass stabilization excipient precipitate, is then calculated based on solubility data for the active agent and glass stabilization excipient in the chosen co-solvent system, respectively, resulting in a co-solvent volume ratio, $R_2$. A preferred embodiment directed to an ethanol/water co-solvent system comprises about 65-95 vol % ethanol and 35-5 vol % water, which is equivalent to $R_2$=1.85-20. A preferred embodiment comprises 70-85 vol % ethanol and 30-15 vol % water, roughly equivalent to $R_2$=2.25-5.75. The feedstock comprising glass stabilization excipient and active agent at ratio $R_1$ and the co-solvent system at ratio $R_2$ is then prepared and spray dried as set forth below. The present invention can be practiced according to this embodiment alone to produce a stable composition of water-insoluble active agent in a glassy matrix, or can be practiced in combination with any of the embodiments discussed below to impart other desirable particle characteristics to the final product.

According to another version, the pharmaceutical formulation particles are engineered to impart desired surface properties to the final particles. According to this embodiment, various surface properties may be effected depending on the intended application of the particulate composition. For particulate compositions intended for pulmonary administration, it may be desirable to provide a dispersibility enhancing coating to the composition. For oral drug delivery applications, it may be desirable to also provide that the particles are readily dispersible to their original primary particles after being formed into an oral dosage form such as a tablet, lozenge, or capsule and the like. Other desired applications may be to provide a tastemasking coating to the particulate compositions, or to provide a coating layer for targeted and/or controlled release of the active agent.

Whatever the intended effect, according to this version, the feedstock is formulated with at least one coating material. The solubility of the active agent in a given co-solvent system is measured as a function of the co-solvent ratio. Based on this solubility data of the active agent and the desired application (including, for example, dispersibility, tastemasking, and/or controlled release), a coating material is selected and the amount of coating material necessary to encapsulate the active agent or modify the particle surface is calculated. This yields an active agent/coating material ratio $R_3$ for the dried particulate. For example, improved dispersibility can be achieved by covering the particle with a thin layer of a suitable surface active excipient. In this case only a small amount of excipient is needed. According to the invention, values for $R_3$ are within 20<R3<1000 in this case. Furthermore improved dispersibility can be achieved by changing the morphology of the particle such that it has a higher rugosity or lower density. In this case the amount of dispersibility enhancer is calculated such that a) it precipitates before the active during the evaporation process and b) is present in sufficient quantity to form a structurally stable shell. According to the invention, values for $R_3$ are within 0.02<R3<50, preferably 0.1<R3<30.

According to this version, incorporating a coating material, the co-solvent system ratio $R_4$ is sufficient to (a) dissolve the desired amount of active agent and coating material provided at ratio $R_3$, such that the coating material is provided in the feedstock within 50% of its saturation concentration, preferably within 25% of its saturation concentration, and to (b) keep the co-solvent ratio close to the initial ratio throughout the course of the evaporation such that the coating material precipitates before the active agent. This ratio $R_4$ is determined based on solubility data and process conditions for the active agent and coating material in the chosen co-solvent system, respectively. According to the preferred embodiment directed to an ethanol/water co-solvent system, the feedstock comprises 65-98 vol % ethanol and 35-2 vol % water roughly equivalent to a volume ratio of ethanol/water $R_4$ of about 1.85-49, preferably 2.25-5.75. The feedstock comprising active agent and coating material at ratio $R_3$ and the co-solvent system at ratio $R_4$ is then prepared and spray dried as discussed below. If it is necessary to increase the $T_g$ of the composition, a glass stabilization excipient is formulated in the feedstock in accordance with the above teachings.

According to a version comprising an ethanol/water co-solvent system, suitable coating materials comprise a solubility in the range of 0.1-40 mg/ml, preferably 0.5-20 mg/ml, more preferably 1-10 mg/ml in the ethanol/water co-solvent system. Dispersibility enhancers for coating the particle include, but are not limited to, the dispersibility enhancing agents listed above. The dispersibility enhancer enables the powders to be readily dispersed from an aerosol delivery device in the case of pulmonary applications, or to readily disperse into primary particles upon contact with an aqueous environment for oral drug delivery applications.

Tastemasking agents to mask the taste of bitter tasting active agents include, but are not limited to, mono-, di-, or polysaccharides, sugar alcohols, or other polyols such as lactose, glucose, raffinose, melezitose, lactitol, mannitol, maltitol, trehalose, sucrose, and starch; ethyl cellulose, methyl cellulose, hydroxypropyl cellulose, hydroxypropyl methylcellulose, hydroxybutyl methylcellulose, cellulose propionate, cellulose acetate propionate, cellulose acetate butyrate, cellulose acetate phthalate, carboxymethyl cellulose, cellulose triacetate, polymethyl methacrylate, polyethyl methacrylate, polyphenyl methacrylate, polymethyl acrylate, polyisopropyl acrylate, polyisobutyl acrylate, polyisobutyl methacrylate, polyhexyl methacrylate, polyphenyl methacrylate, polyvinyl acetate, polyvinyl isobutyl ether, polyvinyl alcohol, polyethylene terephthalate, polyethylene oxide, polyethylene glycol, polyethylene, polypropylene, polyoctadecyl acrylate, polyvinyl chloride, and polyvinyl pyrrolidone. Preferred tastemasking excipients include polyvinyl pyrrolidone, ethyl cellulose, and cellulose acetates. The coating material according to this aspect of the invention may further include at least one plasticizer known in the art such as diethyl phthalate, triethyl citrate, triethyl acetyl citrate, triacetin, tributyl citrate, polyethylene glycol, propylene glycol, glycerol, dibutylsebacate, castor oil, and the like.

Coating materials suitable for oral drug delivery applications that provide for a desired rate or site of release of the active agent are known in the art, as disclosed, for example, in U.S. Pat. Nos. 5,378,474, 5,500,227, 5,648,096, 5,651,990, 5,667,806, 6,149,941, 6,503,927 and PCT WO 98/47493, all of which are incorporated herein by reference in their entireties.

Figure 1A:
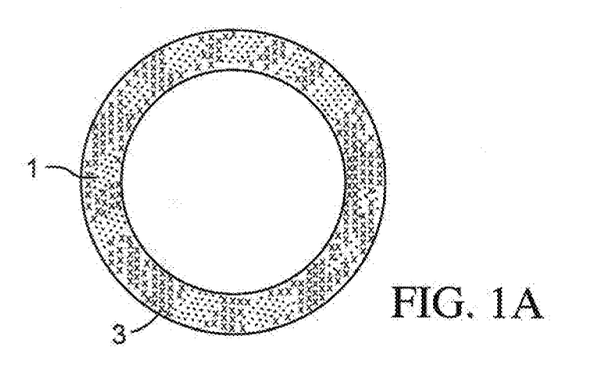
Figure 1B:
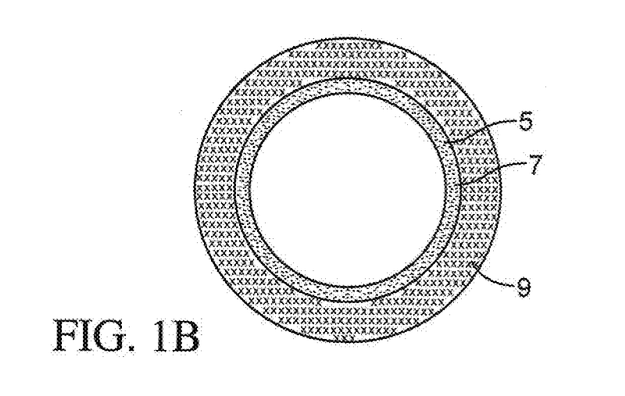
Figure 1C:
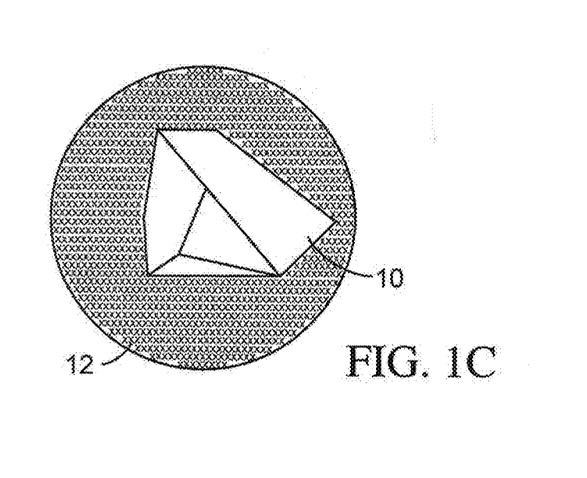

Practice of the present invention results in a number of different particle morphologies, as generally depicted in FIGS. 1a-c. As seen in FIG. 1a, one such particle morphology comprises hollow particles comprising a central void surrounded by an active agent containing layer 1. In order to produce microcapsules as depicted in FIG. 1a, the feedstock comprising active agent 3 and glass stabilization excipient (if required) formulated as set forth above is then spray dried as discussed below. The resultant microcapsules are storage stable as measured by the $T_g$ of the powders. Such microcapsules may be used for a variety of drug delivery applications, including pulmonary, injectable, or oral applications.

According to another version, multi-layered microcapsules as depicted in FIG. 1b are provided. Such particle morphologies result when a coating material is incorporated in the feedstock as set forth above. FIG. 1b depicts a hollow microcapsule comprising a central void which is surrounded by two layers 5 and 9, although additional layers could be incorporated in accordance with the teachings of the present invention. Layer 5 preferably comprises an active agent 7, in crystalline or amorphous form and most preferably comprises an active agent incorporated in a glassy matrix with a glass stabilization excipient. Layer 9 comprises a discrete layer of the selected coating material depending on the desired application.

Another particle morphology is depicted in FIG. 1c. As seen in FIG. 1c, a solid particle is provided wherein a coating material 12 surrounds and encapsulates the active agent 10. The active agent 10 may be in crystalline or non-crystalline or amorphous form. In one version, the active agent is mixed with a glass forming excipient and is in non-crystalline form. The coating layer 12 encapsulates the active agent and may optionally include the active agent or a second active agent.

According to a preferred version, microcapsules of ultrafine dry powders of the type depicted in FIG. 1b are provided. According to this embodiment, inner layer 5 contains an active agent 7, preferably mixed with an amorphous glass stabilization excipient. According to this embodiment, layer 9 contains a dispersibility enhancing excipient which enables the powders to be readily dispersed from an aerosol delivery device.

The present invention may be practiced to produce microcapsules for any number of desired applications and is not limited to pulmonary applications. For example, another preferred embodiment is directed to compositions for oral administration and methods of making such compositions. According to this embodiment, the present invention may be practiced to provide taste-masked compositions and controlled release compositions for oral delivery.

According to this version, the particulate compositions are engineered to comprise an inner core layer comprising the active agent and optional glass stabilization excipients, which layer is at least partially coated with at least one coating material. The glass stabilization excipients are used when it is necessary to increase the $T_g$ of the active agent in accordance with the principles discussed in detail above. If the $T_g$ of the active agent is sufficient by itself, such glass stabilization excipients are not required.

In yet another version, the present invention can be practiced to provide increased bioavailability for insoluble active agents. According to this embodiment, the bioavailability of insoluble molecules is increased when the drug is administered from an amorphous, glassy matrix due to an increase in the drug's solubility and intrinsic dissolution rate. A coating material can be incorporated as set forth above depending on the desired application.

The release profile of the glassy matrix particles can be controlled via the particle size distribution of the glassy matrix. Generally, dissolution rates increase with increased surface area, such that smaller particles result in more rapid dissolution rates. Narrow particle size distributions can be achieved through appropriate atomization and drying, as disclosed in U.S. Pat. Nos. 6,051,256, and published patent applications PCT WO 01/00312 and WO 02/09669, all of which are incorporated by reference herein in their entireties.

Multi-modal particle size distributions to tune-in a desired release profile can be produced in a single spray-drying process by using multiple atomization nozzles as disclosed in PCT Publication WO 01/00312 which is incorporated herein by reference in its entirety.

Another version is directed to increased bioavailability through increased surface area. According to this embodiment, spray drying processes are disclosed which produce particles having a size less than 10 microns, preferably less than 5 microns, and most preferably less than 1 micron in diameter.

Figure 2:
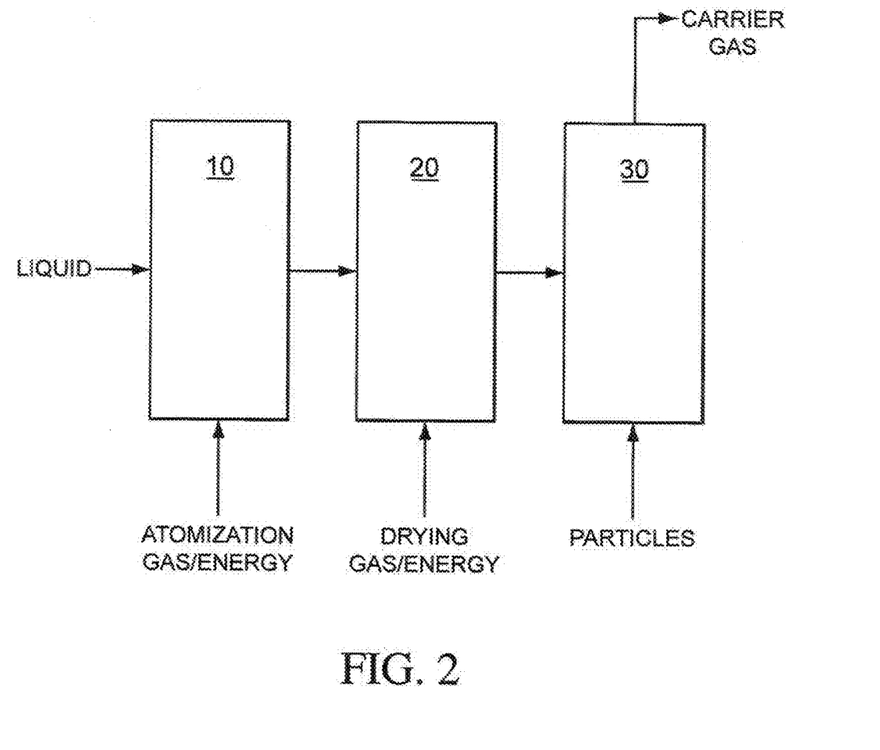

Referring now to FIG. 2, a spray-drying process for preparing powders of water-insoluble active agents according to this invention comprises an atomization operation 10 that produces droplets of a liquid medium, which are subsequently dried in a drying operation 20. The drying operation 20 may be a single drying chamber or a multi-stage operation. Drying of the liquid droplets results in formation of the discrete particles that form the dry powder compositions which are then collected in a separation operation 30. Each of these unit operations is described in greater detail below.

The atomization process 10 may utilize any one of several conventional forms of atomizers. The atomization process increases the surface area of the starting liquid. Due to atomization there is an increase in the surface energy of the liquid, the magnitude of which is directly proportional to the surface area increase. The source of this energy increase depends on the type of atomizer used. Any atomizer (centrifugal, sonic, pressure, two fluid) capable of producing droplets with a mass median diameter of less than about 100 µm, more preferably less than 20 µm could be used. Preferred for the present invention is the use of two fluid atomizers where the liquid medium is delivered through a nozzle concurrently with a high pressure gas stream.

The atomization gas will usually be nitrogen which has been filtered or otherwise cleaned to remove particulates and other contaminants. Alternatively, other gases, such as air may be used. The atomization gas will be pressurized for delivery through the atomization nozzle, typically to a pressure above 5 psig, preferably being above 10 psig. The atomization conditions, including atomization gas flow rate, atomization gas pressure, liquid flow rate, and the like, are controlled to produce liquid droplets having an average diameter below 20 or 10 µm, depending on the embodiment, as measured by phase Doppler particle analysis (PDPA), such as with a Phase Doppler Particle Size Analyzer (Aerometrics). In some embodiments, the atomized droplets have an average diameter in the range from 5 µm to 11 µm, and in one embodiment from 6 µm to 8 µm. In a preferred embodiment, the gas:liquid mass flow ratio may be maintained above 2, preferably in the range from 3 to 15.

The feedstock may be a solution, suspension, colloidal system, or other dispersion of a pharmaceutical in a suitable co-solvent system. In a preferred embodiment, the insoluble active agent is present as a solution in an ethanol/water co-solvent system. Ethanol/water co-solvent systems according to this invention are preferably provided as 65-98 vol % ethanol and 35-2 vol % water as set forth above. Other suitable organic solvents include, but are not limited to, alcohols such as methanol, ketones such as acetone, polar aprotic solvents, hydrogenated hydrocarbons such as metyhlene chloride, hydrocarbons such as cyclohexane, and mixtures thereof. Ethanol is the preferred organic solvent. The total dissolved solids, including the insoluble active agent and other carriers, excipients, etc., that may be present in the final dried particle, may be present at a wide range of concentrations, typically being present at from 0.1% by weight to 10% by weight. Usually, however, it will be desirable to maximize the solids concentration that produces particles in the inhalation size range and has the desired dispersibility characteristics, typically the solids concentration ranges from 0.5% to 10% w/v, more narrowly from 1.0% to 5% w/v. It will thus be understood that the term "feedstock" as used herein is used broadly and encompasses mixtures such as solutions, slurries, suspensions, emulsions, microemulsions, multiple emulsions, and reverse emulsions. Feedstocks containing relatively low concentrations of the active agent will result in dried particulates having relatively small diameters as described in more detail below.

The drying operation 20 is performed next to evaporate liquid from the droplets produced by the atomization operation 10. Usually, the drying includes introducing energy to the droplets, typically by mixing the droplets with a heated gas which causes evaporation of the water or other liquid medium. In one embodiment, the mixing is done in a spray dryer or equivalent chamber where a heated gas stream has been introduced. The heated gas stream may flow concurrently with the atomized liquid, but it would also be possible to employ counter-current flow, cross-current flow, or other flow patterns. It is also possible to perform the drying operation in multiple stages as described in more detail in WO 01/00312 cited above.

The drying operation may be controlled to provide dried particles having particular characteristics, such as a rugosity above 2 as described in U.S. Pat. No. 6,051,256 cited above. Rugosity is a measure of surface convolution, with a higher number indicating a higher degree of surface irregularity. Without intending to limit the scope of the present invention in any way, it is believed that the increase in surface irregularity as measured by rugosity results in a decrease in cohesiveness between adjacent particles. Alternatively, the drying operation may be controlled to produce particles having smooth or substantially smooth surfaces.

The drying rate may be controlled based on a number of variables, including the droplet size distribution, the inlet temperature of the gas stream, the outlet temperature of the gas stream, the inlet temperature of the liquid droplets, and the manner in which the atomized spray and hot drying gas are mixed. In one embodiment, the drying gas stream has an inlet temperature of at least 70° C., and may be at least 120° C., at least 135° C., at least 145° C., and may often be over 175° C., or even as high as 200° C., depending on the active agent being dried. At least in part, the inlet temperature of the heated gas drying stream depends on the lability of the active agent being treated. The outlet temperature is usually in the range of about 50-100° C. The drying gas is moved through the system using conventional blowers or compressors.

The separation operation 30 is selected to achieve very high efficiency collection of the particles produced by the drying operation 20. Conventional separation operations may be used, although in some cases they could be modified to assure collection of submicron particles. In an exemplary embodiment, separation is achieved using a filter medium such as a membrane medium (bag filter), a sintered metal fiber filter, or the like. Alternatively, separation may be achieved using cyclone separators. The separation operation should achieve collection of at least 70% of all particles, and in some embodiments collects more than 85%, more than 90%, or even more than 95% of such particles.

Figure 3:
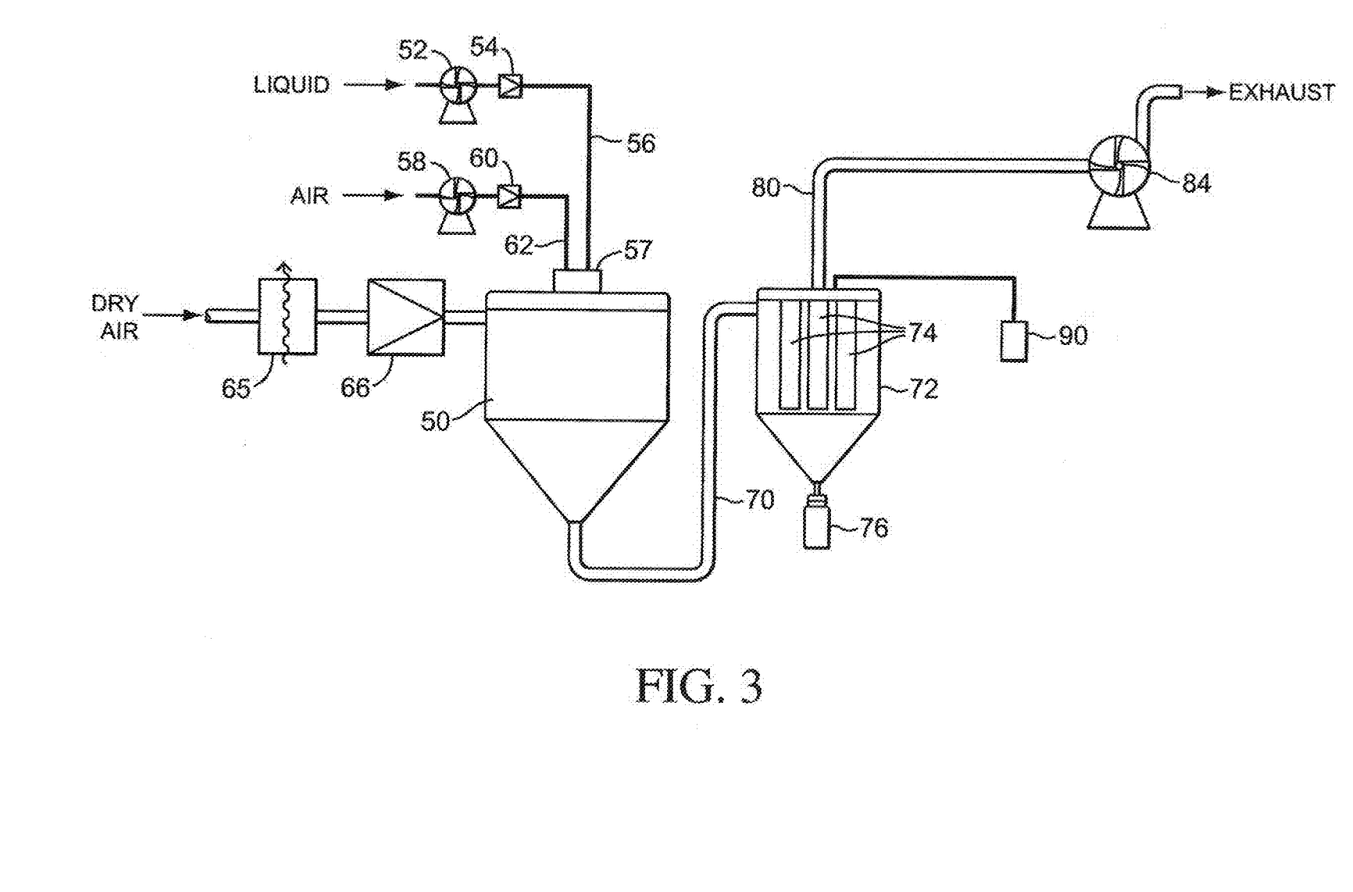

Referring now to FIG. 3, an exemplary spray-dryer system is described. The system includes a spray dryer 50, which may be a commercial spray dryer such as those available from suppliers such as Buchi, Niro, APV, Yamato Chemical Company, Okawara Kakoki Company, and others. The spray dryer 50 is provided with a feedstock as described above through a supply pump 52, filter 54, and supply line 56. The supply line 56 is connected to a multi-nozzle two-fluid atomizer 57. Atomizing air is supplied from a compressor 58, a filter 60, and line 62 to the atomizer 57. Drying air is also provided to the spray dryer 50 through a heater 65 and a filter 66.

Dried particles from the spray dryer 50 are carried by the air flow through conduit 70 to a filter housing 72. The filter housing 72 includes a plurality of internal filter elements 74, which may be bag filters or sintered metal fiber filters, such as sintered stainless steel fiber filters of the type described in Smale, Manufacturing Chemist, p. 29, April 1992. Alternative filter media comprise bag filters, cloth filters, and cartridge filters. In all cases, the gas stream carrying the dried particles flows into the shell of separator housing 72, and the carrier gas passes through the filter elements 74. Passage of the dried particles, however, is blocked by the filter elements, and the dried particles fall by gravity to the bottom of the housing 72 where they are collected in a particle collection canister 76. The canister 76 may periodically be removed and replaced, and the dry powder in the canister 76 used for packaging in unit dosage or other forms. The carrier gas passes out from the top of the separator housing 72 through line 80 and an exhaust fan 84. The filters 82 collect any particles that may inadvertently pass through the filter media 74. A source 90 of high-pressure gas is provided for periodically producing a pulsed flow of counter-current air through the filter media 74. Such pulsed air flow in the reverse direction dislodges particles that adhere to the inlet side of the filter medium to prevent caking.

The invention is further illustrated in greater detail with the aid of the following examples without being restricted thereto:

EXAMPLE 1

Coated budesonide particles were designed, which employed L-Leucine as coating material. Based on the solubilities of L-Leucine and Budesonide in the ethanol water system, L-Leucine is effective in coating the budesonide at a co-solvent volume ratio, R4, of 5.7 (85% vol ethanol), and an active to coating material ratio, R3, of 4.7 (82.5% Budesonide/17.5% L-Leucine). Particles were prepared by a spray drying process according to the invention. 603.68 mg of budesonide (Industriale Chimica s.c.l., #502595) and 128.03 mg of L-Leucine (Sigma, # L-8000) were dissolved in 87.7 g of an ethanol water mixture with 85% vol of ethanol, The resulting solution was utilized as the feedstock for spray-drying on a B-190 Mini Spray-Drier (Büchi, Flawil, Switzerland). The following spray conditions were employed: aspiration=100%, inlet temperature=85° C., outlet temperature=60° C., feed pump=5 mL min$^{-1}$, atomizer pressure=40 psig, atomizer gas flow rate=0.2 scfm, total gas flow rate=14 scfm.

Figure 4:
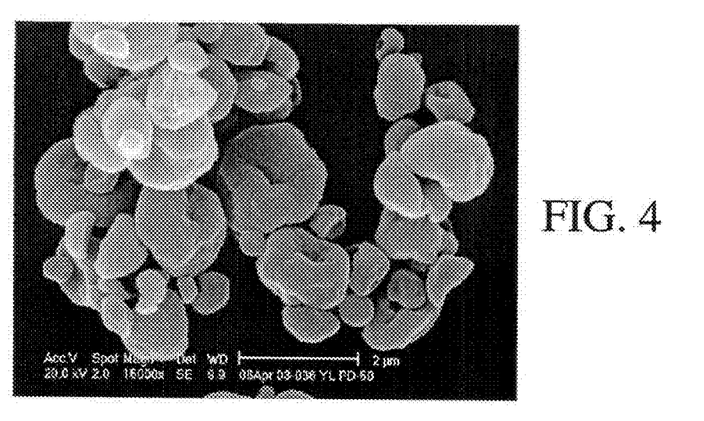

FIG. 4 shows a scanning electro micrograph (SEM) of the resulting particles. The particles have an irregular surface and corresponding high rugosity, indicating successful coating of the budesonide.

Figure 5:
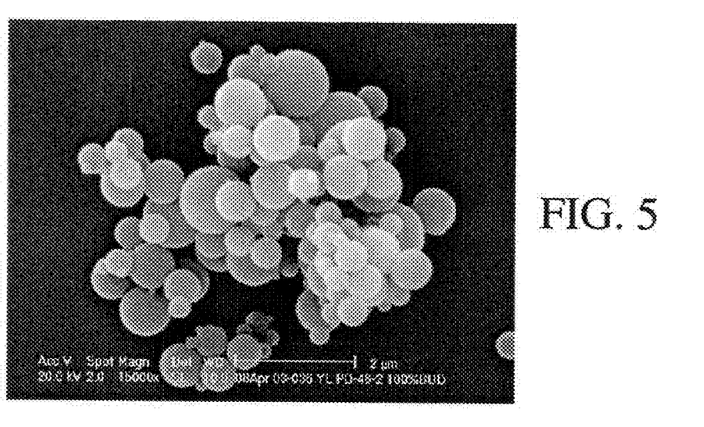

For comparison, neat budesonide was spray dried from an ethanol water co-solvent system with a co-solvent volume ratio, R4, of 5.7 (85% vol ethanol) under the same processing conditions set forth above. FIG. 5 is an SEM depicting the particles. As seen in FIG. 5, budesonide forms spherical particles with a low rugosity when spray dried without excipients. The particles are spherical with a smooth surface and some fusing of particles can be observed. These properties are less desirable for a dry powder formulation intended for pulmonary drug delivery.

As a further comparison, budesonide-leucine particles were prepared using the same active to coating material ratio, R3, of 4.7 (82.5% Budesonide/17.5% L-Leucine) as above, but using a co-solvent volume ratio, R4, of 1 (50% vol ethanol). Based on the solubilities of L-Leucine and Budesonide in the ethanol water system, L-Leucine is not effective in coating the budesonide at this co-solvent volume ratio. Under these conditions the budesonide is expected to dominate the particle formation. The particles were prepared according to the following procedure. 605.65 mg of budesonide (Industriale Chimica s.c.l., #502595) and 129.5 mg of L-Leucine (Sigma, # L-8000) were dissolved in, 97.2 g of an ethanol water mixture with 50% vol of ethanol, The resulting solution was utilized as the feedstock for spray-drying on a B-190 Mini Spray-Drier (Büchi, Flawil, Switzerland). The following spray conditions were employed: aspiration=100%, inlet temperature=85° C., outlet temperature56° C., feed pump rate=5 mL min$^{-1}$, atomizer pressure=40 psig, atomizer gas flow rate=0.2 scfm, total gas flow rate=14 scfm.

Figure 6:
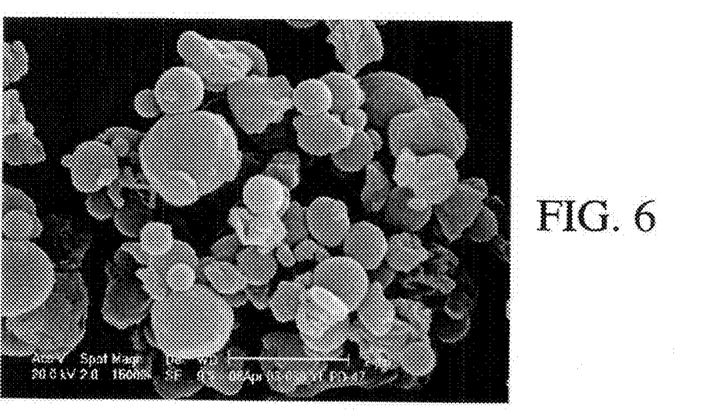

FIG. 6 shows that under these conditions the L-leucine is effective in coating the budesonide, but less effective than in the version shown in FIG. 4. Some of the particles retain a smooth spherical morphology with low rugosity.

EXAMPLE 2

Coated budesonide particles were designed, which employed L-Leucine as coating material. Three lots, A, B, and C with an active agent to coating material ratio, R3, of 4.7 were manufactured.

Two of the lots, B and C, had a co-solvent volume ratio, R4, of 3. Based on the solubilities of L-Leucine and Budesonide in the ethanol water system, L-Leucine is effective in coating the budesonide at this co-solvent volume ratio. Lot C was spray-dried with increased solids content in the feed solution of 12.5 mg/ml compared to 7 mg/ml for lots B and A. During the course of the evaporation the co-solvent volume ratio decreases due to preferential evaporation of ethanol. Increasing the solids content of the feed solution shifts the precipitation of the dispersibility enhancer to earlier stages in the evaporation process. Thus, the co-solvent volume ratio at the point of precipitation is higher for lot C than for lot B, improving the effectiveness of the dispersibility enhancer.

Lot A served as a control. It had a co-solvent volume ratio, R4, of 1 (50% vol ethanol). Based on the solubilities of L-Leucine and Budesonide in the ethanol water system, L-Leucine is effective, but not as effective in coating the budesonide at this co-solvent volume ratio.

Particles were prepared by a spray drying process according to the invention, using the same processing parameters as given in Example 1.

The lots were analyzed for surface composition using X-ray Photoelectron Spectroscopy. Powder dispersibility was tested using a passive dry powder inhaler (DPI), such as the passive DPI inhaler described in U.S. Pat. No. 4,995,385 which is incorporated herein by reference in its entirety. The test was performed by connecting a vacuum system to the mouthpiece of the DPI. The vacuum system was controlled to provide airflow through the DPI similar to human inhalation with regard to volume and flow rate. 15 mg of powder was filled into capsules and loaded into the DPI. After dispersion in the DPI the aerosol was drawn into an Anderson Cascade Impactor and the Mass Median Aerodynamic Diameter (MMAD) and the fraction of particles with an aerodynamic diameter less than 3.3 µm (FPF<3.3 µm) were determined gravimetrically.

Table 1 shows the results of the analyses. The lots with the more effective co-solvent volume ratio (B and C) had an increased L-Leucine surface concentration relative to the control lot A. The L-Leucine enrichment was more than 200% for B and C. Increasing the solids content in the feed solution had the expected effect of further improving the effectiveness of encapsulation. The MMAD of the lots with the more effective co-solvent volume ratio (B and C) was decreased relative to the control lot, demonstrating that improved dispersibility was achieved by increasing the L-Leucine surface concentration. This is confirmed by an increase in FPF<3.3 µm for these lots. Lot C was spray-dried with a higher solids content in the feed solution, which leads to an approximately 20% larger aerodynamic particle diameter of the individual dry particles. However, the aerosol MMAD was further reduced relative to lot B and the FPF<3.3 µm was increased. This shows that the increase in L-Leucine enrichment on the surface relative to lot B improved the dispersibility of the powder further.

TABLE 1

| Lot Identifier | A | B | C |
|---|---|---|---|
| Mass fraction of Budesonide in the formulation | 0.825 | 0.825 | 0.825 |
| Mass fraction of L-Leucine in the formulation | 0.175 | 0.175 | 0.175 |
| Coating material ratio, R3 | 4.71 | 4.71 | 4.71 |
| Vol % ethanol in the co-solvent | 50 | 75 | 75 |
| Co-solvent volume ratio, R4 | 1 | 3 | 3 |
| Solids content in the feed solution | 7 mg/ml | 7 mg/ml | 12.5 mg/ml |
| Surface mass fraction of L-Leucine by XPS | 0.3 | 0.39 | 0.46 |
| Leucine enrichment on the surface | 171% | 221% | 260% |
| MMAD | 4.5 µm | 3.8 µm | 3.7 µm |
| FPF < 3.3 µm | 31% | 37% | 41% |

Although the present invention has been described in considerable detail with regard to certain preferred versions thereof, other versions are possible, and alterations, permutations and equivalents of the version shown will become apparent to those skilled in the art upon a reading of the specification and study of the drawings. For example, the cooperating components may be reversed or provided in additional or fewer number. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. A method of preparing a pharmaceutical formulation, the method comprising:
   providing a solution comprising a first solvent, a second solvent, an active agent, and an excipient, wherein the second solvent is less polar than the first solvent, wherein the excipient is more soluble in the first solvent than the active agent, and wherein the excipient comprises an amino acid; and
   removing the first and second solvents to produce particles comprising the active agent and the excipient, wherein the particles have a mass median diameter less than 5 µm.

2. A method according to claim 1 wherein the particles each comprise the active agent and the excipient.

3. A method according to claim 1 wherein the particles comprise excipient encapsulating the active agent.

4. A method according to claim 1 wherein the first and second solvents are removed by spray drying.

5. A method according to claim 1 wherein the excipient comprises one or more of alanine, leucine, and trileucine.

6. A method according to claim 1 wherein the excipient comprises leucine or trileucine.

7. A method according to claim 1 wherein the ratio of second solvent to first solvent is greater than 1.

8. A method according to claim 1 wherein the ratio of second solvent to first solvent is about 80:20.

9. A method according to claim 1 wherein the first solvent is water.

10. A method according to claim 1 wherein the second solvent comprises a hydroxylic solvent.

11. A method according to claim 1 wherein the second solvent comprises a C1-C6 alcohol.

12. A method according to claim 1 wherein the second solvent comprises acetone.

13. A method according to claim 1 wherein the active agent has a solubility in water less than 1 mg/ml and wherein the excipient has a solubility in water greater than 1 mg/ml.

14. A method of preparing an aerosolizable pharmaceutical formulation, the method comprising:
providing a solution comprising a first solvent, a second solvent, an active agent, and an excipient, wherein the second solvent is less polar than the first solvent and wherein the excipient is more soluble in water than the active agent; and removing the first and second solvents to produce particles comprising the active agent and the excipient, wherein at least 20% of the particles have an aerodynamic diameter less than 3.3 μm when determined gravimetrically in an Anderson Cascade Impactor, wherein the particles have a mass median diameter less than 5 μm.

15. A method according to claim 14 wherein the excipient comprises an amino acid and/or a phospholipid.

16. A method according to claim 14 wherein the excipient comprises leucine or trileucine.

17. A method of preparing a pharmaceutical formulation, the method comprising:

providing a solution comprising water, a hydroxylic solvent, an active agent, and an excipient, wherein the excipient comprises leucine or trileucine and is more soluble in water than the active agent; and removing the first and second solvents to produce particles comprising the active agent and the excipient, wherein the particles have a mass median diameter less than 5 μm.

18. A method according to claim 17 wherein the particles each comprise the active agent and the excipient.

19. A method according to claim 17 wherein the particles comprise excipient encapsulating the active agent.

20. A method according to claim 17 herein the first and second solvents are removed by spray drying.

21. A method according to claim 17 wherein the ratio of hydroxylic solvent to water is greater than 1.

22. A method according to claim 17 wherein the second solvent comprises ethanol.

23. A method according to claim 1 wherein the particles further comprise a phospholipid.

* * * * *